(12) United States Patent
McCarthy

(10) Patent No.: US 8,168,869 B2
(45) Date of Patent: May 1, 2012

(54) SWEET PEPPER HYBRID 9930417

(75) Inventor: William McCarthy, Ft. Myers, FL (US)

(73) Assignee: Seminis Vegetable Seeds, Inc., Woodland, CA (US)

(*) Notice: Subject to any disclaimer, the term of this patent is extended or adjusted under 35 U.S.C. 154(b) by 377 days.

(21) Appl. No.: 12/604,301

(22) Filed: Oct. 22, 2009

(65) Prior Publication Data

US 2010/0115655 A1 May 6, 2010

Related U.S. Application Data

(60) Provisional application No. 61/109,847, filed on Oct. 30, 2008.

(51) Int. Cl.
*A01H 5/00* (2006.01)
*A01H 5/08* (2006.01)
*A01H 5/10* (2006.01)
*A01H 1/02* (2006.01)
*C12N 5/04* (2006.01)

(52) U.S. Cl. .............. 800/317.1; 800/265; 800/278; 435/430.1

(58) Field of Classification Search .............. None
See application file for complete search history.

(56) References Cited

U.S. PATENT DOCUMENTS 8,049,077 B2 * 11/2011 Leij .............................. 800/317.1

OTHER PUBLICATIONS

PI 632919 (Charleston Belle) deposited 2002.*
U.S. Appl. No. 12/604,302, filed Oct. 22, 2009, McCarthy.
U.S. Appl. No. 12/604,314, filed Oct. 22, 2009, McCarthy.
Berke, "Hybrid seed production in Capsicum," Journal of New Seeds, 1 (3/4): 49-67, 1999.
Pickersgill et al., "Genetic resources and breeding of Capsicum spp.," Euphytica, 96:129-133, 1997.

* cited by examiner

*Primary Examiner* — David T Fox
(74) *Attorney, Agent, or Firm* — SNR Denton US LLP; Alissa Eagle, Esq.

(57) ABSTRACT

The invention provides seed and plants of pepper hybrid 9930417 and the parent lines thereof. The invention thus relates to the plants, seeds and tissue cultures of pepper hybrid 9930417 and the parent lines thereof, and to methods for producing a pepper plant produced by crossing such plants with themselves or with another pepper plant, such as a plant of another genotype. The invention further relates to seeds and plants produced by such crossing. The invention further relates to parts of such plants, including the fruit and gametes of such plants.

31 Claims, No Drawings

SWEET PEPPER HYBRID 9930417

CROSS-REFERENCE TO RELATED APPLICATIONS

This application claims the priority of U.S. provisional application Ser. No. 61/109,847, filed Oct. 30, 2008, the disclosure of which is specifically incorporated herein by reference.

FIELD OF THE INVENTION

The present invention relates to the field of plant breeding and, more specifically, to the development of pepper hybrid 9930417 and of the inbred pepper lines SBR99-1243 and SBY99-1179.

BACKGROUND OF THE INVENTION

The goal of vegetable breeding is to combine various desirable traits in a single variety/hybrid. Such desirable traits may include greater yield, resistance to insects or pests, tolerance to heat and drought, better agronomic quality, higher nutritional value, growth rate and fruit properties.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different genotypes produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines and hybrids produced therefrom are evaluated to determine which of those have commercial potential.

SUMMARY OF THE INVENTION

In one aspect, the present invention provides a pepper plant of the hybrid designated 9930417 and/or pepper lines SBR99-1243 and SBY99-1179. Also provided are pepper plants having all the physiological and morphological characteristics of the pepper hybrid 9930417. Parts of the sweet pepper plant of the present invention are also provided, for example, including pollen, an ovule, a scion, a rootstock, a fruit, and a cell of the plant.

The invention also concerns the seed of pepper hybrid 9930417 and/or pepper lines SBR99-1243 and SBY99-1179. The pepper seed of the invention may be provided as an essentially homogeneous population of pepper seed of pepper hybrid 9930417 and/or pepper lines SBR99-1243 and SBY99-1179. Essentially homogeneous populations of seed are generally free from substantial numbers of other seed. Therefore, seed of hybrid 9930417 and/or pepper lines SBR99-1243 and SBY99-1179 may be defined as forming at least about 97% of the total seed, including at least about 98%, 99% or more of the seed. The seed population may be separately grown to provide an essentially homogeneous population of pepper plants designated 9930417 and/or pepper lines SBR99-1243 and SBY99-1179.

In another aspect of the invention, a plant of pepper hybrid 9930417 and/or pepper lines SBR99-1243 and SBY99-1179 comprising an added heritable trait is provided. The heritable trait may comprise a genetic locus that is, for example, a dominant or recessive allele. In one embodiment of the invention, a plant of pepper hybrid 9930417 and/or pepper lines SBR99-1243 and SBY99-1179 is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of the line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

In another aspect of the invention, a tissue culture of regenerable cells of a pepper plant of hybrid 9930417 and/or pepper lines SBR99-1243 and SBY99-1179 is provided. The tissue culture will preferably be capable of regenerating pepper plants capable of expressing all of the physiological and morphological characteristics of the starting plant from which tissue is obtained, and of regenerating plants having substantially the same genotype as the starting plant. Examples of some of the physiological and morphological characteristics of the hybrid 9930417 and/or pepper lines SBR99-1243 and SBY99-1179 include those traits set forth in the tables herein. The regenerable cells in such tissue cultures may be derived, for example, from embryos, meristems, cotyledons, pollen, leaves, anthers, roots, root tips, pistil, flower, seed and stalks. Still further, the present invention provides pepper plants regenerated from a tissue culture of the invention, the plants having all the physiological and morphological characteristics of hybrid 9930417 and/or pepper lines SBR99-1243 and SBY99-1179.

In yet another aspect of the invention, processes are provided for producing pepper seeds, plants and fruit, which processes generally comprise crossing a first parent pepper plant with a second parent pepper plant, wherein at least one of the first or second parent pepper plants is a plant of pepper lines SBR99-1243 and SBY99-1179. These processes may be further exemplified as processes for preparing hybrid pepper seed or plants, wherein a first pepper plant is crossed with a second pepper plant of a different, distinct genotype to provide a hybrid that has, as one of its parents, a plant of pepper line SBR99-1243 or pepper line SBY99-1179. In these processes, crossing will result in the production of seed. The seed production occurs regardless of whether the seed is collected or not.

In one embodiment of the invention, the first step in "crossing" comprises planting seeds of a first and second parent pepper plant, often in proximity so that pollination will occur, for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent pepper plants into plants that bear flowers. A third step may comprise preventing self-pollination of the plants, such as by emasculating the flowers (i.e., killing or removing the pollen). Self-incompatibility systems may also be used in some hybrid crops for the same purpose. Self-incompatible plants still shed viable pollen and can pollinate plants of other varieties but are incapable of pollinating themselves or other plants of the same genotype.

A fourth step for a hybrid cross may comprise cross-pollination between the first and second parent pepper plants. Yet another step comprises harvesting the seeds from at least one of the parent pepper plants. The harvested seed can then be grown to produce a pepper plant.

The present invention also provides the pepper seeds and plants produced by a process that comprises crossing a first parent pepper plant with a second parent pepper plant, wherein at least one of the first or second parent pepper plants is a plant of pepper hybrid 9930417 and/or pepper lines SBR99-1243 and SBY99-1179. In one embodiment of the invention, pepper seed and plants produced by the process are first generation ($F_1$) hybrid pepper seed and plants produced by crossing a plant in accordance with the invention with another, distinct plant. The present invention further contemplates plant parts of such an $F_1$ hybrid pepper plant, and methods of use thereof. Therefore, certain exemplary embodiments of the invention provide an $F_1$ hybrid pepper plant and seed thereof.

In still yet another aspect, the present invention provides a method of producing a plant derived from hybrid 9930417 and/or pepper lines SBR99-1243 and SBY99-1179, the method comprising the steps of: (a) preparing a progeny plant derived from hybrid 9930417 and/or pepper lines SBR99-1243 and SBY99-1179, wherein said preparing comprises crossing a plant of the hybrid 9930417, pepper line SBR99-1243, or pepper line SBY99-1179 with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from hybrid 9930417, pepper line SBR99-1243, or pepper line SBY99-1179. The plant derived from hybrid 9930417 and/or pepper lines SBR99-1243 and SBY99-1179 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from hybrid 9930417 and/or pepper lines SBR99-1243 and SBY99-1179 is obtained which possesses some of the desirable traits of the starting plant as well as potentially other selected traits.

In certain embodiments, the present invention provides a method of producing peppers comprising: (a) obtaining a plant of pepper hybrid 9930417 and/or pepper lines SBR99-1243 and SBY99-1179, wherein the plant has been cultivated to maturity, and (b) collecting peppers from the plant.

In still yet another aspect of the invention, the genetic complement of pepper hybrid 9930417 and/or pepper lines SBR99-1243 and SBY99-1179 is provided. The phrase "genetic complement" is used to refer to the aggregate of nucleotide sequences, the expression of which sequences defines the phenotype of, in the present case, a pepper plant, or a cell or tissue of that plant. A genetic complement thus represents the genetic makeup of a cell, tissue or plant, and a hybrid genetic complement represents the genetic make up of a hybrid cell, tissue or plant. The invention thus provides pepper plant cells that have a genetic complement in accordance with the pepper plant cells disclosed herein, and plants, seeds and plants containing such cells.

Plant genetic complements may be assessed by genetic marker profiles, and by the expression of phenotypic traits that are characteristic of the expression of the genetic complement, e.g., isozyme typing profiles. It is understood that hybrid 9930417 and/or pepper lines SBR99-1243 and SBY99-1179 could be identified by any of the many well known techniques such as, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

In still yet another aspect, the present invention provides hybrid genetic complements, as represented by pepper plant cells, tissues, plants, and seeds, formed by the combination of a haploid genetic complement of a pepper plant of the invention with a haploid genetic complement of a second pepper plant, preferably, another, distinct pepper plant. In another aspect, the present invention provides a pepper plant regenerated from a tissue culture that comprises a hybrid genetic complement of this invention.

In still yet another aspect, the invention provides a plant that exhibits a combination of traits comprising a sturdy, medium-sized, anthocyaninless plant, with excellent cover; a plant that produces a heavy set of fruit that are uniform, smooth and of similar size, and which mature from green to red, and often weighs between 280 and 300 grams, and appears resistant or tolerant to races 1, 2 and 3 of Bacterial Leaf Spot (*Xanthomonas campestris* pv. *vesicatoria*), Tobamovirus (P0) and *Phytopthora capsici*. In certain embodiments, the combination of traits may be defined as controlled by genetic means for the expression of the combination of traits found in pepper hybrid 9930417.

In still yet another aspect, the invention provides a method of determining the genotype of a plant of pepper hybrid 9930417 and/or pepper lines SBR99-1243 and SBY99-1179 comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

Any embodiment discussed herein with respect to one aspect of the invention applies to other aspects of the invention as well, unless specifically noted.

The term "about" is used to indicate that a value includes the standard deviation of the mean for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The invention provides methods and compositions relating to plants, seeds and derivatives of sweet pepper hybrid 9930417. The invention also provides parent lines SBR99-1243 and SBY99-1179.

In one embodiment, a plant of the invention comprises one or more improved traits, selected from a sturdy, medium-sized, anthocyaninless plant with excellent cover; a plant that produces a heavy set of fruit that are uniform, smooth and of similar size, and which mature from green to red, and often weigh between 200 and 250 grams, and appears resistant or tolerant to races 1, 2 and 3 of Bacterial Leaf Spot (*Xanthomonas campestris* pv *vesicatoria*), Tobamovirus (P0), and *Phytophtora capsici*. The development of hybrid 9930417 and its parent lines can be summarized as follows.

A. Origin and Breeding History of Pepper Hybrid 9930417

The parents of sweet pepper hybrid 9930417 are pepper line SBR99-1243 and pepper line SBY99-1179.

Line SBR99-1243 was developed by pedigree selection from a double-haploid event from a cross between inbred lines SBR27-136 and E8646.98LB 3043-1. The inbred SBR99-1243 develops an anthocyaninless, semi-spreading, medium-sized plant that produces medium green fruit that mature to red. The large smooth fruit possess a rather deep profile (length:width approximately 1.1).

The female parent, SBR 27-136, developed into a medium-sized plant that produced a good set of early maturing, medium to large fruit. Fruit were green maturing to red, rather ribby with a good side wall. The line is resistant to the Tobacco mosaic virus pathotype P0 [TMV(P0)] via the L1 gene. The male parent, E8646.98LB 3043-1, was a heavy-setting line that produced a large, square, anthocyaninless fruit that was segregating for red and yellow fruit color. The line was resistant to races 1, 2, and 3 Bacterial leaf spot [(*Xanthomonas campestris* pv. *vesicatoria*) Bs2 gene].

SBR99-1243 differs from SBR 27-136 because it is anthocyaninless and susceptible to the TMV(P0) whereas SBR 27-136 is not anthocyaninless and is resistant to TMV(P0). SBR99-1243 differs from E8646.98LB 3043-1 because it is fixed for red fruit color and is susceptible to races 1, 2, and 3 BLS whereas E8646.98LB 3043-1 was segregating for mature fruit color (red/yellow) and was resistant to races 1, 2, and 3 BLS.

The crossing and selections were made as follows:

Year 1: Planted and crossed the inbred lines SBR 27-136 and E8646.98LB 3043-1 to produce the hybrid "99BK".

Year 1: The hybrid 99BK was sent to a tissue culture facility. Anthers were cultured and double haploid plants were produced (DH0). The double haploid plants were allowed to self pollinate and produce seed.

Year 2: Planted the DH1 line 99DH BK-09-M as stake 02LB 01942. The line was tested for resistance to the Tobacco mosaic virus pathotype $P_0$ (L1 gene) and found to be susceptible. The line was tested for resistance to the Tomato spotted wilt virus (Tswv gene) and found it to be susceptible. The line was tested for resistance to the Tobamovirus (L4 gene) and found it to be susceptible. The line was tested for race 1, 2, and 3 BLS (Bs2 gene) resistance and found it to be susceptible. The line appeared uniform and stable. Entire plot harvested and bulked.

Year 3: Planted DH2 seed of 02LB 01942-M inbred line as stake #02LB 08150. The line produced very small, leafy plants which produced a heavy set of medium green fruit that matured red. The line appeared uniform and stable.

Year 3: Planted DH2 seed of 02LB 01942-M inbred line as stake #02LB 12977. The line produced medium large, branchy plants which provided good cover. The plants produced a rather early maturing fruit of good size and shape. The line appeared uniform and stable.

Year 4: Planted DH2 seed of 02LB 01942-M inbred line as stake #03LB 09150. The line produced medium large plants with small leaves that produced square-shaped fruit with a medium green color. The line appeared uniform and stable. The source 02LB 01942-M was submitted as parent "SBR99-1243".

SBR99-1243 has been observed as uniform and stable over two generations and is within commercially acceptable limits. As is true with other sweet pepper inbreds, a small percentage of variants can occur within commercially acceptable limits for almost any characteristic during the course of repeated multiplication.

A description of the physiological and morphological characteristics of pepper line SBR99-1243 is presented in Table 1.

TABLE 1

Physiological and Morphological Characteristics of Line SBR99-1243 and a Selected Variety

| | Characteristic | SBR99-1243 | Early Cal Wonder |
|---|---|---|---|
| 1 | Species | *C. annuum* | *C. annuum* |
| 2 | Maturity in region of most adaptability | | |
| | Days from transplanting until mature green stage | 66 | 67 |
| | Days from transplanting until mature red or yellow stage | 87 | 85 |
| | Days from direct seeding until mature green stage | 106 | 104 |
| | Days from direct seeding until mature red or yellow stage | 127 | 122 |
| 3 | Plant | | |
| | Habit | Semi-spreading | Compact |
| | Attitude | Semi-erect | Erect |
| | Plant height | 58.4 cm | 63.5 cm |
| | Plant width | 43.2 cm | 55.9 cm |

TABLE 1-continued

Physiological and Morphological Characteristics
of Line SBR99-1243 and a Selected Variety

| | Characteristic | SBR99-1243 | Early Cal Wonder |
|---|---|---|---|
| | Length of stem from cotyledon to first flower | 15.0 cm | 17.8 cm |
| | Length of the third internode (from soil surface) | 86.4 cm | 69.9 cm |
| | Basal branches | Few (2-3) | Few (2-3) |
| | Branch flexibility | Rigid (Yolo Wonder L) | Rigid (Yolo Wonder L) |
| | Stem strength (breakage resistance) | Intermediate | Intermediate |
| 4 | Leaf | | |
| | Leaf width | 44.5 mm | 42.0 mm |
| | Leaf length | 88.9 mm | 80.0 mm |
| | Petiole length | 57.7 mm | 30.0 mm |
| | Mature leaf shape | Elliptic | Elliptic |
| | Color | Medium Green | Medium Green |
| | Color (RHS color chart value) | 139A | 143A |
| | Leaf and stem pubescence | Absent (Yolo Wonder L) | Absent (Yolo Wonder L) |
| | Margin undulation | Absent | Absent |
| | Blistering | Medium | Medium |
| 5 | Flowers | | |
| | Number of flowers per leaf axil | 1 | 1 |
| | Calyx (calyx lobes) | 6 | 6 |
| | Petals | 6 | 7 |
| | Diameter | 25.4 mm | 25.0 mm |
| | Corolla color | White | White |
| | Corolla throat markings | Yellow (tan) | Yellow (tan) |
| | Anther color | Yellow | Purple |
| | Style length | Same as stamen | Less than stamen |
| | Self-incompatibility | Absent | Absent |
| 6 | Fruit | | |
| | Group | Bell (Yolo Wonder L) | Bell (Yolo Wonder L) |
| | Immature fruit color | Medium Green (Long Thin Cayenne) | Medium Green (Long Thin Cayenne) |
| | Immature fruit color (RHS Color Chart value) | 144A | 137A |
| | Mature fruit color | Red (Yolo Wonder L) | Red (Yolo Wonder L) |
| | Mature fruit color (RHS Color Chart Value) | 46B | 46A |
| | Pungency | Sweet (Yolo Wonder L) | Sweet (Yolo Wonder L) |
| | Flavor | Mild Pepper Flavor | Moderate Pepper Flavor |
| | Fruit glossiness | Shiny | Moderate |
| | Surface smoothness | Smooth (Yolo Wonder L) | Smooth (Yolo Wonder L) |
| | Fruit position | Pendent (Jalapeno) | Pendent (Jalapeno) |
| | Calyx shape | Saucer-shaped (Flat, non-enveloping) | Saucer-shaped (Flat, non-enveloping) |
| | Calyx diameter | 38.1 mm | 32.0 mm |
| | Fruit length | 95.3 mm | 80.0 mm |
| | Fruit diameter at calyx attachment | 76.2 mm | 70.0 mm |
| | Fruit diameter at mid-point | 88.9 mm | 80.0 mm |
| | Flesh thickness at mid-point | 6.4 mm | 6.0 mm |
| | Average number of fruits per plant | 15.0 | 10.0 |
| | % Large fruits | Weight range: 175 to 240 g (17.0%) | Weight Range: 130 to 200 g (50.0%) |
| | % Medium fruits | Weight range: 130 to 160 g (50.0%) | Weight range: 90 to 120 g (30.0%) |
| | % Small fruits | Weight range: 80 to 120 g (33.0%) | Weight range: 50 to 75 g (20.0%) |
| | Average fruit weight | 139.7 gm | 100.0 gm |
| | Base shape | Cupped (Yolo Wonder L) | Cupped (Yolo Wonder L) |
| | Apex shape | Blunt (Yolo Wonder L) | Blunt (Yolo Wonder L) |
| | Shape | Bell (Yolo Wonder L) | Bell (Yolo Wonder L) |
| | Longitudinal section | Square | Square |
| | Cross section at level of placenta | Quadrangular | Quadrangular |
| | Fruit set | Concentrated | Concentrated |
| | Interloculary grooves | Medium | Medium |
| | Fruits with one locule | 0.0% | 0.0% |
| | Fruits with two locules | 0.0% | 0.0% |
| | Fruits with three locules | 43.0% | 40.0% |
| | Fruits with four locules | 53.0% | 60.0% |
| | Fruits with five or more locules | 4.0% | 0.0% |
| | Average number of locules | 3.6 | 3.6 |
| | Pedicel length | 44.5 mm | 20.0 mm |
| | Pedical thickness | 6.4 mm | 6.0 mm |
| | Pedicel shape | Curved | Curved |
| | Pedicel cavity | Absent | Absent |
| 7 | Seed | | |
| | Cavity length | 76.2 mm | 43.0 mm |
| | Cavity diameter | 69.9 mm | 52.0 mm |
| | Placenta length | 38.1 mm | 22.0 mm |
| | Number of seeds per fruit | 206 | 100 |
| | Weight per 1000 seeds | 8.3 gm | 7.5 gm |
| | Seed color | Yellow | Yellow |
| 8 | Anthocyanin | | |
| | Seeding hypocotyl | Absent | Weak |
| | Stem | Absent | Weak |
| | Node | Weak | Moderate |
| | Leaf | Absent | Absent |
| | Pedical | Absent | Absent |
| | Calyx | Absent | Absent |
| | Fruit | Absent | Moderate |

*These are typical values. Values may vary due to environment. Other values that are substantially equivalent are also within the scope of the invention.

SBY99-1179 was developed by pedigree selection from Seminis hybrid SVR 7273802. This hybrid resulted from the cross between female "Y79?7488Y" and male "SBY29-469".

SBY99-1179 develops an anthocyaninless, small to medium-sized plant that provides heavy cover. The plant produces a firm, weak green-maturing to yellow fruit with good shape and a nice shoulder. Tests indicate the line is fixed for resistance to the Tobacco etch virus (TEV) (pvr2-2 gene), fixed for Tobacco mosaic virus (pathotype P0) (TMV) resistance (L1 gene), fixed for resistance to races 1, 2, and 3 bacterial spot (BLS)[(*Xanthomonas campestris* pv. *vesicatoria*) Bs2 gene], and resistant or tolerant to *Phytopthora capsici*.

Parent "Y79?7488Y" was a blocky, yellow bell segregating for the anthocyaninless trait, fixed for resistance to TEV, fixed for resistance to TMV, and fixed for resistance to races 1, 2, and 3 BLS. Parent "SBY29-469" was an anthocyaninless, yellow, blocky bell fixed for TEV resistance, fixed for TMV resistance, and resistant or tolerant to *Phytopthora capsici*. Neither parent was marketed directly as open pollinated lines. SBY99-1179 differs from Y79?7488Y because it is fixed for the anthocyaninless trait and is resistant or tolerant to *P. capsici*. SBY99-1179 differs from SBY29-469 because it is resistant to TMV and is resistant to races 1, 2, and 3 BLS.

The crossing and selections were made as follows:

Year 1: Planted parents "Y79?7488Y" as inbred #LBGH 3251 and "SBY29-469" as inbred # LBGH 3294. The $F_1$ Hybrid SVR 7273802 was made.

Year 2: Sowed $F_1$ hybrid SVR 7273802 as stake #98LB 5151. The hybrid was selfed and massed.

Year 2: Planted $F_2$ inbred line 98LB 5151-M as stake #98LB YBS 388. Individual plants were selected.

Year 3: Planted $F_3$ inbred line 95LB YBS 388-01 as stake #99LB 1181. The line was segregating for low level resistance to *P. capsici*. Individual plants were selected.

Year 3: Planted $F_4$ inbred line 99LB 1181-01 as stake #99LB 7173. The line was fixed for TMV resistance, fixed for TEV resistance, and fixed for resistance to races 1, 2, and 3 BLS. Notes also indicate the line was segregating to *P. capsici*. Individual plants were selected.

Year 4: Planted $F_5$ inbred line 99LB 7173-01 as stake #00LB 2171. The line was segregating for low level resistance to *P. capsici*. Individual plants were selected.

Year 4: Submitted $F_6$ inbred line 00LB 2171-01 to pathology to screen for resistance to *P. capsici* as pathology test line WM 85395. Resistant survivors were saved.

Year 5: Planted $F_7$ inbred line WM 85395-51 as stake #01LB 7797. Small plants with firm fruit and weak fruit color were produced. Individual plants were selected.

Year 6: Planted $F_8$ inbred line 01LB 7797-04 as stake #02LB 04011. Anthocyaninless, yellow-fruited line with a small to medium plant that provided heavy cover were produced. Further, line produced firm fruit, with good shape and a nice shoulder, and weak green fruit color. Tests indicate the line was fixed for resistance to the Tobacco etch virus (pvr2-2 gene), fixed for TMV resistance, fixed for resistance to races 1, 2, and 3 BLS and resistant to *P. capsici*. Plants were stable and uniform. The line was bulked.

Year 6: The inbred line, 02LB 004011-M, was designated SBY99-1179.

SBY99-1179 has been observed as uniform and stable over two generations, and it is within commercially acceptable limits. As is true with other sweet pepper inbreds, a small percentage of variants can occur within commercially acceptable limits for almost any characteristic during the course of repeated multiplication. However, no known variants were observed during the 26 times that SBY99-1179 was observed in field trials.

A description of the physiological and morphological characteristics of pepper line SBY99-1179 is presented in Table 2.

TABLE 2

Physiological and Morphological Characteristics of Line SBY99-1179 and a Selected Variety

| CHARACTERISTIC | SBY99-1179 | Early Cal Wonder |
|---|---|---|
| 1 Species | C. annuum | C. annuum |
| 2 Maturity in region of most adaptability | | |
| Days from transplanting until mature green stage) | 71 | 67 |
| Days from transplanting until mature red or yellow stage) | 92 | 85 |
| Days from direct seeding until mature green stage) | 108 | 104 |
| Days from direct seeding until mature red or yellow stage) | 129 | 122 |
| 3 Plant | | |
| Habit | compact | compact |
| Attitude | upright/erect (De Cayenne, Doux trés long des Landes, Piquant d'Algerie) | upright/erect (De Cayenne, Doux trés long des Landes, Piquant d'Algerie) |
| Plant height | 36.9 cm | 40.9 cm |
| Plant width | 41.1 cm | 47.1 cm |
| Length of stem from cotyledon to first flower | 11.2 cm | 10.7 cm |
| Length of the third internode (from soil surface) | 60.7 mm | 54.0 mm |
| Length of stem | medium (Belsir, Lamuyo) | |
| Shortened internode (in upper part) | absent (California wonder, De Cayenne) | |
| Length of internode (on primary side shoots) | short (Bandero, Blondy, Danubia, Tenor) | |
| Stem: Hairiness of nodes | absent or very weak (Arlequin) | |
| Height | short (Albaregia) | |
| Basal branches | none | few (2-3) |
| Branch flexibility | rigid (Yolo Wonder) | rigid (Yolo Wonder) |
| Stem strength (breakage resistance) | strong | intermediate |
| 4 Leaf | | |
| Length of blade | long (Cupido, Dolmy, Encore, Mazurka, Monte) | |
| Width of blade | medium (Albaregia, Balaton, Danubia, Marconi, Merit) | |
| Leaf width | 56.3 mm | 60.0 mm |
| Leaf length | 100.3 mm | 113.3 mm |
| Petiole length | 34.3 mm | 46.0 mm |
| Color | dark green | light green |
| Color (RHS Color Chart value) | 137A | 147A |
| Intensity of green color | dark (Dolmy, Tinto) | |
| Mature leaf shape | ovate (Balico, Sonar) | ovate (Balico, Sonar) |
| Leaf and stem pubescence | absent | absent |
| Undulation of margin | absent (De Cayenne) | absent (De Cayenne) |
| Blistering | weak (Pusztagold) | weak (Pusztagold) |
| Profile in cross section | flat (De Cayenne) | |
| Glossiness | weak (De Cayenne, Doux trés long des Landes) | |
| Peduncle: Attitude | erect (Fehér, Red Chilli) | |
| 5 Flower | | |
| Number of flowers per leaf axil | 1 | 1 |
| Number of calyx lobes | 6 | 6 |
| Number of petals | 6 | 6 |
| Diameter | 22.4 mm | 25.1 mm |
| Corolla color | white | white |
| Corolla throat markings | yellow | yellow |
| Anther color | yellow | purple |
| Style Length | less than stamen | same as stamen |
| Self-incompatibility | absent | absent |

TABLE 2-continued

Physiological and Morphological Characteristics of Line SBY99-1179 and a Selected Variety

| CHARACTERISTIC | SBY99-1179 | Early Cal Wonder |
|---|---|---|
| Fruit | | |
| Group | Bell (Yolo Wonder L.) | Bell (Yolo Wonder L.) |
| Color before maturity | green (California wonder, Lamuyo) | |
| Intensity of color (before maturity) | medium | |
| Immature fruit color | medium green | medium green |
| Immature fruit color (RHS Color Chart value) | green 143A | green 137A |
| Attitude/position | drooping/pendent (De Cayenne, Lamuyo) | drooping/pendent (De Cayenne, Lamuyo) |
| Length | medium (Fehér, Lamuyo) | |
| Diameter | medium (Doux italien, Corno di toro) | |
| Ratio length/diameter | small (Bucano, Topgirl) | |
| Calyx diameter | 29.0 mm | 32.0 mm |
| Fruit length | 76.5 mm | 80.0 mm |
| Fruit diameter at calyx attachment | 69.7 mm | 70.0 mm |
| Fruit diameter at mid-point | 77.3 mm | 80.0 mm |
| Flesh thickness at mid-point | 6.4 mm | 6.0 mm |
| Average number of fruits per plant | 12.7 | 10.0 |
| % large fruits | Weight range: 200 to 300 g (7.2%) | Weight range: 130 to 200 g (50.0%) |
| % medium fruits | Weight range: 100 to 195 g (19.7%) | Weight range: 90 to 120 g (30.0%) |
| % small fruits | Weight range: 5 to 95 g (73.1%) | Weight range: 50 to 75 g (20.0%) |
| Average fruit weight | 96.3 gm | 100.0 gm |
| Shape in longitudinal section | square (Delphin, Yolo Wonder) | square (Delphin, Yolo Wonder) |
| Shape in cross section (at level of placenta) | quadrangular | quadrangular |
| Sinuation of pericarp at basal part | very weak (Delphin, Kalocsai V-2, Milord) | |
| Sinuation of pericarp excluding basal part | weak (Clovis, Sonar) | |
| Texture of surface | smooth or very slightly wrinkled (Milord) | smooth or very slightly wrinkled (Milord) |
| Color (at maturity) | yellow (Golden calwonder, Heldor) | |
| Intensity of color (at maturity) | medium | |
| Mature fruit color | orange-yellow | red |
| Mature fruit color (RHS Color Chart value) | yellow orange 17C | 46A |
| Glossiness | medium/moderate (Carré doux extra hâtif, Lamuyo, Sonar) | medium/moderate (Carré doux extra hâtif, Lamuyo, Sonar) |
| Stalk cavity | present (Bingor, Lamuyo) | |
| Depth of stalk cavity | very shallow (Flush, Kaméleon, Niagara) | |
| Pedicel length | 33.5 mm | 20.0 mm |
| Pedicel thickness | 9.7 mm | 6.0 mm |
| Pedicel shape | curved | curved |
| Pedicel cavity | present | absent |
| Depth of pedicel cavity | 4.0 mm | |
| Stalk: Length | medium (Fehér, Sonar) | |
| Stalk: Thickness | medium (Doux italien, Surpas) | |
| Base shape | cupped | cupped |
| Shape of apex | moderately depressed (Quadrato a'Asti rosso) | very depressed (Kerala, Monte, Osir) |
| Shape | Bell (Yolo Wonder L.) | Bell (Yolo Wonder L.) |
| Fruit set | concentrated | scattered |
| Depth of interloculary grooves | medium (Clovis, Lamuyo, Marconi) | medium (Clovis, Lamuyo, Marconi) |
| Number of locules | predominantly four and more (Palio, PAZ szentesi) | |
| Fruits with one locule | 0.0% | 0.0% |
| Fruits with two locules | 6.0% | 0.0% |
| Fruits with three locules | 21.2% | 40.0% |
| Fruits with four locules | 69.7% | 60.0% |
| Fruits with five or more locules | 3.1% | 0.0% |
| Average number of locules | 3.69 | 3.6 |
| Thickness of flesh | thick (Andevalo, Bingor, Daniel, Topgirl) | |
| Calyx: Aspect | non-enveloping/saucer-shaped (Lamuyo, Sonar) | non-enveloping/saucer-shaped (Lamuyo, Sonar) |
| Pungency | sweet | sweet |
| Capsaicin in placenta | absent (Sonar) | |
| Flavor | mild pepper flavor | moderate pepper flavor |
| Glossiness | moderate | shiny |
| Seed | | |
| Seed cavity length | 58.9 mm | 43.0 mm |
| Seed cavity diameter | 63.0 mm | 52.0 mm |
| Placenta length | 19.3 mm | 22.0 mm |
| Number of seeds per fruit | 132 | 100 |
| Grams per 1000 seeds | 7.8 gm | 7.5 gm |
| Color | yellow | yellow |
| Plant | | |
| Seedling: Anthocyanin coloration of hypocotyl | absent (Albaregia, Albena) | moderate |
| Anthocyanin coloration of stem | absent | absent |
| Anthocyanin coloration of nodes | absent (Albaregia) | weak |
| Intensity of anthocyanin coloration of nodes | very weak | |
| Anthocyanin coloration of leaf | absent | absent |
| Anthocyanin coloration of pedicel | absent | absent |
| Anthocyanin coloration of calyx | absent | absent |
| Anthocyanin coloration in anther | absent (Danza) | |
| Anthocyanin coloration | absent (Lamuyo) | absent (Lamuyo) |
| Beginning of flowering (1st flower on 2nd flowering node) | medium (Lamuyo, Latino) | |
| Time of maturity | medium (Lamuyo, Latino, Sonar) | |

*These are typical values. Values may vary due to environment. Other values that are substantially equivalent are also within the scope of the invention.

B. Physiological and Morphological Characteristics of Pepper Hybrid 9930417

In accordance with one aspect of the present invention, there is provided a plant having the physiological and morphological characteristics of pepper hybrid 9930417. A description of the physiological and morphological characteristics of pepper hybrid 9930417 is presented in Table 3.

TABLE 3

Physiological and Morphological Characteristics of Hybrid 9930417 and a Selected Variety

| | CHARACTERISTIC | 9930417 | Early Cal Wonder |
|---|---|---|---|
| 1 | Species | C. annuum | C. annuum |
| 2 | Maturity in region of most adaptability | | |
| | Days from transplanting until mature green stage | 71 | 67 |
| | Days from transplanting until mature red or yellow stage | 88 | 85 |
| | Days from direct seeding until mature green stage | 108 | 104 |
| | Days from direct seeding until mature red or yellow stage | 125 | 122 |
| 3 | Plant | | |
| | Habit | compact | compact |
| | Attitude | upright/erect (De Cayenne, Doux très long des Landes, Piquant d'Algérie) | upright/erect (De Cayenne, Doux très long des Landes, Piquant d'Algérie) |
| | Plant height | 30.8 cm | 40.9 cm |
| | Plant width | 37.7 cm | 47.1 cm |
| | Length of stem from cotyledon to first flower | 12.8 cm | 10.7 cm |
| | Length of the third internode (from soil surface) | 89.5 mm | 54.0 mm |
| | Length of stem | short (Delphin, Trophy) | |
| | Shortened internode (in upper part) | absent (California wonder, De Cayenne) | |
| | Length of internode (on primary side shoots) | short (Bandero, Blondy, Danubia, Tenor) | |
| | Stem: Hairiness of nodes | absent or very weak (Arlequin) | |
| | Height | medium (HRF) | |
| | Basal branches | none | few (2-3) |
| | Branch flexibility | rigid (Yolo Wonder) | rigid (Yolo Wonder) |
| | Stem strength (breakage resistance) | intermediate | intermediate |
| 4 | Leaf | | |
| | Length of blade | long (Cupido, Dolmy, Encore, Mazurka, Monte) | |
| | Width of blade | broad (California wonder, Golden calwonder, Seifor, Solario) | |
| | Leaf width | 58.7 mm | 60.0 mm |
| | Leaf length | 101.7 mm | 113.3 mm |
| | Petiole length | 55.6 mm | 46.0 mm |
| | Color | dark green | light green |
| | Color (RHS Color Chart value) | green 137B | 147A |
| | Intensity of green color | dark (Dolmy, Tinto) | |
| | Mature leaf shape | ovate (Balico, Sonar) | ovate (Balico, Sonar) |
| | Leaf and stem pubescence | absent | absent |
| | Undulation of margin | very weak | absent |
| | Blistering | medium (Merit) | weak (Pusztagold) |
| | Profile in cross section | moderately concave (Doux italien, Favolor) | |
| | Glossiness | medium (Alby, Eolo) | |
| | Peduncle: Attitude | erect (Fehér, Red Chili) | |
| 5 | Flower | | |
| | Number of flowers per leaf axil | 1 | 1 |
| | Number of calyx lobes | 6 | 6 |
| | Number of petals | 6 | 6 |
| | Diameter | 26.1 mm | 25.1 mm |
| | Corolla color | white | white |
| | Corolla throat markings | yellow | yellow |
| | Anther color | yellow | purple |
| | Style Length | less than stamen | same as stamen |
| | Self-incompatibility | absent | absent |
| 6 | Fruit | | |
| | Group | Bell (Yolo Wonder L.) | Bell (Yolo Wonder L.) |
| | Color before maturity | green (California wonder, Lamuyo) | |
| | Intensity of color (before maturity) | dark | |
| | Immature fruit color | dark green | medium green |
| | Immature fruit color (RHS Color Chart value) | green 144A | green 137A |
| | Attitude/position | drooping/pendent (De Cayenne, Lamuyo) | drooping/pendent (De Cayenne, Lamuyo) |
| | Length | medium (Fehér, Lamuyo) | |
| | Diameter | broad (Clovis, Lamuyo) | |
| | Ratio length/diameter | very small (Liebesapfel, PAZ szentesi, Rotopa) | |
| | Calyx diameter | 31.3 mm | 32.0 mm |
| | Fruit length | 83 mm | 80.0 mm |
| | Fruit diameter at calyx attachment | 75.3 mm | 70.0 mm |
| | Fruit diameter at mid-point | 76.5 mm | 80.0 mm |
| | Flesh thickness at mid-point | 7.0 mm | 6.0 mm |
| | Average number of fruits per plant | 11.1 | 10.0 |
| | % large fruits | 20.7% (weight range: 140 g to 200 g) | 50.0% (weight range: 130 g to 200 g) |
| | % medium fruits | 33.40% (weight range: 80 g to 135 g) | 30.0% (weight range: 90 g to 120 g) |
| | % small fruits | 45.9% (weight range: 5 g to 75 g) | 20.0% (weight range: 50 g to 75 g) |
| | Average fruit weight | 97.9 gm | 100.0 gm |
| | Shape in longitudinal section | square (Delphin, Yolo Wonder) | square (Delphin, Yolo Wonder) |
| | Shape in cross section (at level of placenta) | quadrangular | quadrangular |
| | Sinuation of pericarp at basal part | weak (Donat) | |
| | Sinuation of pericarp excluding basal part | weak (Clovis, Sonar) | |

TABLE 3-continued

Physiological and Morphological Characteristics
of Hybrid 9930417 and a Selected Variety

| CHARACTERISTIC | 9930417 | Early Cal Wonder |
|---|---|---|
| Texture of surface | smooth or very slightly wrinkled (Milord) | smooth or very slightly wrinkled (Milord) |
| Color (at maturity) | red (Fehér, Lamuyo) | |
| Intensity of color (at maturity) | dark | |
| Mature fruit color | red | red |
| Mature fruit color (RHS Color Chart value) | red 46A | 46A |
| Glossiness | medium/moderate (Carré doux extra hâtif, Lamuyo, Sonar) | medium/moderate (Carré doux extra hâtif, Lamuyo, Sonar) |
| Stalk cavity | present (Bingor, Lamuyo) | |
| Depth of stalk cavity | very shallow (Flush, Kaméleon, Niagara) | |
| Pedicel length | 28.8 mm | 20.0 mm |
| Pedicel thickness | 9.9 mm | 6.0 mm |
| Pedicel shape | curved | curved |
| Pedicel cavity | present | absent |
| Depth of pedicel cavity | 1.0 mm | |
| Stalk: Length | medium (Fehér, Sonar) | |
| Stalk: Thickness | thick (Lamuyo, Trophy Palio) | |
| Base shape | cupped | cupped |
| Shape of apex | very depressed (Kerala, Monte, Osir) | very depressed (Kerala, Monte, Osir) |
| Shape | Bell (Yolo Wonder L.) | Bell (Yolo Wonder L.) |
| Fruit set | concentrated | scattered |
| Depth of interloculary grooves | medium (Clovis, Lamuyo, Marconi) | medium (Clovis, Lamuyo, Marconi) |
| Number of locules | predominantly four and more (Palio, PAZ szentesi) | |
| Fruits with one locule | 0% | 0% |
| Fruits with two locules | 3.4% | 0% |
| Fruits with three locules | 33.4% | 40.0% |
| Fruits with four locules | 63.2% | 60.0% |
| Fruits with five or more locules | 0% | 0% |
| Average number of locules | 3.60 | 3.6 |
| Calyx: Aspect | non-enveloping/ saucer-shaped (Lamuyo, Sonar) | non-enveloping/ saucer-shaped (Lamuyo, Sonar) |
| Pungency | sweet | sweet |
| Capsaicin in placenta | absent (Sonar) | |
| Flavor | strong pepper flavor | moderate pepper flavor |
| Glossiness | moderate | shiny |
| 7 Seed | | |
| Seed cavity length | 65.2 mm | 43.0 mm |
| Seed cavity diameter | 61.3 mm | 52.0 mm |
| Placenta length | 24.4 mm | 22.0 mm |
| Number of seeds per fruit | 288 | 100 |
| Grams per 1000 seeds | 5.0 gm | 7.5 gm |
| Color | yellow | yellow |
| 8 Plant | | |
| Seedling: Anthocyanin coloration of hypocotyl | absent (Albaregia, Albena) | moderate |
| Anthocyanin coloration of stem | absent | absent |
| Anthocyanin coloration of nodes | weak | weak |
| Stem: Intensity of anthocyanin coloration of nodes | very weak | |
| Anthocyanin coloration of leaf | absent | absent |
| Anthocyanin coloration of pedicel | absent | absent |
| Anthocyanin coloration of calyx | absent | absent |
| Flower: Anthocyanin coloration in anther | absent (Danza) | |
| Fruit: Anthocyanin coloration | absent (Lamuyo) | |
| Beginning of flowering (1st flower on 2nd flowering node) | early (Carré doux extra hâtif, Cupido, Fehér, Flaviano, Lito, Trophy) | |
| Time of maturity | early (Fehér, Lady Bell, Topgirl) | |

*These are typical values. Values may vary due to environment. Other values that are substantially equivalent are also within the scope of the invention.

The parents of hybrid 9930417, lines SBR99-1243 and SBY99-1179, being substantially homozygous, can be reproduced by planting seeds of the lines, growing the resulting pepper plants under self-pollinating or sib-pollinating conditions and harvesting the resulting seeds using techniques familiar to one of skill in the art.

C. Breeding Pepper Plants

One aspect of the current invention concerns methods for crossing the sweet pepper hybrid 9930417 and/or pepper lines SBR99-1243 and SBY99-1179, with itself or a second plant and the seeds and plants produced by such methods. These methods can be used for propagation of pepper hybrid 9930417 and/or pepper lines SBR99-1243 and SBY99-1179, or can be used to produce hybrid pepper seeds and the plants grown therefrom. Hybrid seeds are produced by crossing hybrid 9930417 and/or pepper lines SBR99-1243 and SBY99-1179 with a plant of a different genotype as well as by selfing a hybrid.

The development of new varieties using one or more starting varieties is well known in the art. In accordance with the invention, novel varieties may be created by crossing hybrid 9930417 and/or pepper lines SBR99-1243 and SBY99-1179, followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with hybrid 9930417 and/or pepper lines SBR99-1243 and SBY99-1179, and progeny thereof to achieve a homozygous line.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny have the characteristic being transferred, but are like the superior parent for most or almost all other loci. The last backcross generation would be selfed to give pure breeding progeny for the trait being transferred.

Various genes and conferring insect resistance are also known in the art and could be introduced into a pepper plant in accordance with the invention. Insect pests affecting the various species of pepper include the European corn borer, corn earworm, aphids, flea beetles, whiteflies, and mites (Midwest Vegetable Production Guide for Commercial Growers, 2003).

D. Performance Characteristics

As described above, hybrid 9930417 exhibits desirable agronomic traits, including a sturdy, medium-sized, anthocyaninless plant, with excellent cover; a plant that produces a heavy set of fruit that are uniform, smooth and of similar size, and which mature from green to red, and often weigh between 200 and 250 grams; and a plant that appears resistant or tolerant to races 1, 2 and 3 of Bacterial Leaf Spot (*Xanthomonas campestris* pv. *vesicatoria*), Tobamovirus (P0) and *Phytopthora capsici*. These and other performance characteristics of the hybrid were the subject of an objective analysis of the performance traits relative to other varieties. The results of the analysis are presented below.

TABLE 4

Performance Characteristics For Hybrid 9930417

| Variety | Source | Race 1-3 BLS resistance (Bs2 gene) | PVY(P0) resistance | Antho-cyaninless | Fruit color at green harvest | Fruit size width (cm) × length (cm) | Fruit weight (g.) |
|---|---|---|---|---|---|---|---|
| 9930417 (Prophet) | Seminis | yes | no | yes | Light medium | 8 × 9 | 225 |
| Baron | Seminis | no | no | yes | medium | 9 × 9 | 220 |
| Excalibur | Seminis | no | no | no | dark | 9 × 10 | 240 |
| Wizard X3R | Seminis | yes | yes | no | dark | 10 × 10 | 260 |
| Aristotle | Seminis | yes | yes | yes | medium | 10 × 11 | 280 |
| Crusader | Syngenta | yes | yes | no | dark | 10 × 10 | 260 |
| Affinity | Syngenta | no | no | no | medium | 9 × 10 | 250 |
| Jupiter | Syngenta | no | no | no | medium | 9 × 9 | 200 |

The plants of the present invention are particularly well suited for the development of new lines based on the elite nature of the genetic background of these plants. In selecting a second plant to cross with 9930417 and/or pepper lines SBR99-1243 and SBY99-1179 for the purpose of developing novel pepper lines, it will typically be preferred to choose those plants which either themselves exhibit one or more selected desirable characteristics or which exhibit the desired characteristic(s) when in hybrid combination. Examples of desirable traits of sweet peppers include: high seed yield, high seed germination, seedling vigor, early fruit maturity, high fruit yield, ease of fruit setting, disease tolerance or resistance, and adaptability for soil and climate conditions. Consumer-driven traits, such as a preference for a given fruit size, shape, color, texture, and taste, especially non-pungency (low capsaicinoid content), are other traits that may be incorporated into new lines of sweet pepper plants developed by this invention.

Particularly desirable traits that may be incorporated by this invention is improved resistance to different viral, fungal, and bacterial pathogens. Anthracnose and Phytophthora blight are fungal diseases affecting various species of pepper. Fruit lesions and fruit rot are the commercially important aspects of these diseases. Bacterial leaf spot and bacterial wilt are other diseases affecting pepper plants, especially during the wet season. Viral pathogens affecting pepper plants include the pepper mosaic virus and the tobacco mosaic virus.

As shown above, hybrid 9930417 combines resistance to Bacterial Leaf Spot Races 1 to 3, anthocyaninless growth, light medium fruit color, and more a desirable fruit size and weight when compared to competing varieties. One important aspect of the invention thus provides seed of the variety for commercial use.

E. Further Embodiments of the Invention

In one embodiment of the invention, plants are provided of pepper hybrid 9930417 and/or pepper lines SBR99-1243 and SBY99-1179 modified to include at least a first desired heritable trait. Such plants may, in particular embodiments, be developed by a plant breeding technique called backcrossing, wherein essentially all of the desired morphological and physiological characteristics of a variety are recovered in addition to a genetic locus transferred into the plant via the backcrossing technique. The term single locus converted plant as used herein refers to those pepper plants which are developed by a plant breeding technique called backcrossing, wherein essentially all of the desired morphological and physiological characteristics of a variety are recovered in addition to the single locus transferred into the variety via the backcrossing technique.

Backcrossing methods can be used with the present invention to improve or introduce a characteristic into the present variety. The parental pepper plant which contributes the locus for the desired characteristic is termed the nonrecurrent or donor parent. This terminology refers to the fact that the nonrecurrent parent is used one time in the backcross protocol and therefore does not recur. The parental pepper plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a pepper plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele, or an additive allele (between recessive and dominant), may also be transferred. In this instance it may be necessary to introduce a test of the progeny to determine if the desired characteristic has been successfully transferred.

In one embodiment, progeny pepper plants of a backcross in which 9930417 is the recurrent parent comprise (i) the desired trait from the non-recurrent parent and (ii) all of the physiological and morphological characteristics of pepper hybrid 9930417 as determined at the 5% significance level when grown in the same environmental conditions.

Pepper varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and enhanced nutritional quality. These comprise genes generally inherited through the nucleus.

Direct selection may be applied where the single locus acts as a dominant trait. An example of a dominant trait is a gene conferring resistance to cucumber mosaic virus (WO 2001/084912). For this selection process, the progeny of the initial cross are assayed for viral resistance and/or the presence of the corresponding gene prior to the backcrossing. Selection eliminates any plants that do not have the desired gene and resistance trait, and only those plants that have the trait are used in the subsequent backcross. This process is then repeated for all additional backcross generations.

Selection of pepper plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection applicable to the breeding of pepper are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

F. Plants Derived by Genetic Engineering

Many useful traits that can be introduced by backcrossing, as well as directly into a plant, are those which are introduced by genetic transformation techniques. Genetic transformation may therefore be used to insert a selected transgene into a pepper plant of the invention or may, alternatively, be used for the preparation of transgenes which can be introduced by backcrossing. Methods for the transformation of plants, including pepper plants, are well known to those of skill in the art (see, e.g., Schroeder et al., 1993). Techniques which may be employed for the genetic transformation of pepper plants include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

*Agrobacterium*-mediated transformation of pepper explant material and regeneration of whole transformed pepper plants (including tetraploids) from the transformed shoots has been shown to be an efficient transformation method (U.S. Pat. No. 5,262,316).

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target pepper cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994), and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for pepper plant gene expression include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly duplicated version of the CaMV 35S promoter, the enhanced 35S promoter (P-e35S) the nopaline synthase promoter (An et al., 1988), the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane baciliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wunI, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to the pepper plants of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a pepper plant according to the invention. Non-limiting examples of particular genes and corresponding phenotypes one may choose to introduce into a pepper plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

G. Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing, wherein essentially all of the desired morphological and physiological characteristics of a pepper variety/line are recovered in addition to the characteristics of the single locus transferred in via the backcrossing technique and/or by genetic transformation.

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant.

Transgene: A genetic locus comprising a sequence which has been introduced into the genome of a pepper plant by transformation.

H. Deposit Information

A deposit of pepper hybrid 9930417 and inbred parent line SBR99-1243, disclosed above and recited in the claims, has been made with the American Type Culture Collection (ATCC), 10801 University Blvd., Manassas, Va. 20110-2209. The deposits were made on May 30, 2008. The accession numbers for those deposited seeds of pepper hybrid 9930417 and inbred parent line SBR99-1243 are ATCC Accession Number PTA-9223 and ATCC Accession Number PTA-9227, respectively. Upon issuance of a patent, all restrictions upon the deposits will be removed, and the deposits are intended to meet all of the requirements of 37 C.F.R. §1.801-1.809. The deposits will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

REFERENCES

The following references, to the extent that they provide exemplary procedural or other details supplementary to those set forth herein, are specifically incorporated herein by reference:

U.S. Pat. No. 5,262,316
U.S. Pat. No. 5,378,619
U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,880,275
U.S. Pat. No. 7,087,819
An et al., *Plant Physiol.*, 88:547, 1988.
Berke, *J. New Seeds*, 1:3-4, 1999.
Bird et al., *Biotech. Gen. Engin. Rev.*, 9:207, 1991.
Bustos et al., *Plant Cell*, 1:839, 1989.
Callis et al., *Plant Physiol.*, 88:965, 1988.
Chae et al., *Capsicum Eggplant Newsltr.*, 22:121-124, 2003.
Choi et al., *Plant Cell Rep.*, 13: 344-348, 1994.

Dekeyser et al., *Plant Cell*, 2:591, 1990.
Ellul et al., *Theor. Appl. Genet.*, 107:462-469, 2003.
EP 534 858
Fraley et al., *Bio/Technology*, 3:629-635, 1985.
Fromm et al., *Nature*, 312:791-793, 1986.
Fromm et al., *Plant Cell*, 1:977, 1989.
Gibson and Shillito, *Mol. Biotech.*, 7:125, 1997
Klee et al., *Bio-Technology*, 3(7):637-642, 1985.
Kuhlemeier et al., *Plant Cell*, 1:471, 1989.
Marcotte et al., *Nature*, 335:454, 1988.
Marcotte et al., *Plant Cell*, 1:969, 1989.
Midwest Veg. Prod. Guide for Commercial Growers (ID:56), 2003
Odel et al., *Nature*, 313:810, 1985.
Omirulleh et al., *Plant Mol. Biol.*, 21(3):415-428, 1993.
Pandal et al., *Theor. Appl. Gene.*, 68(6):567-577, 1984.
Pickersgill and Barbara, *Euphytica*, 96(1):129-133, 1997
Potrykus et al., *Mol. Gen. Genet.*, 199:183-188, 1985.
Roshal et al., *EMBO J.*, 6:1155, 1987.
Schaffner and Sheen, *Plant Cell*, 3:997, 1991.
Schernthaner et al., *EMBO J.*, 7:1249, 1988.
Siebertz et al., *Plant Cell*, 1:961, 1989.
Simpson et al., *EMBO J.*, 4:2723, 1985.
Terada and Shimamoto, *Mol. Gen. Genet.*, 220:389, 1990.
Uchimiya et al., *Mol. Gen. Genet.*, 204:204, 1986.
Wang et al., *Science*, 280:1077-1082, 1998.
Williams et al., *Nucleic Acids Res.*, 18:6531-6535, 1990.
WO 99/31248
WO 01/084912

What is claimed is:

1. A pepper plant comprising at least a first set of the chromosomes of pepper line SBR99-1243, a sample of seed of said line having been deposited under ATCC Accession Number PTA-9227.

2. A pepper seed comprising at least a first set of the chromosomes of pepper line SBR99-1243, a sample of seed of said line having been deposited under ATCC Accession Number PTA-9227.

3. The pepper plant of claim 1, which is inbred.

4. The pepper plant of claim 1, which is hybrid.

5. The pepper plant of claim 4, wherein the hybrid plant is a plant of pepper hybrid 9930417, a sample of seed of said hybrid 9930417 having been deposited under ATCC Accession Number PTA-9223.

6. The pepper plant of claim 3, wherein the inbred plant is pepper line SBR99-1243.

7. A pepper plant part of the plant of claim 1.

8. The plant part of claim 7, further defined as a leaf, a ovule, pollen, a fruit, or a cell.

9. A pepper plant, or a part thereof, having all the physiological and morphological characteristics of the pepper plant of claim 5.

10. A pepper plant, or a part thereof, having all the physiological and morphological characteristics of the pepper plant of claim 6.

11. A tissue culture of regenerable cells of the pepper plant of claim 1.

12. The tissue culture according to claim 11, comprising cells or protoplasts from a pepper plant part selected from the group consisting of embryos, meristems, cotyledons, pollen, leaves, anthers, roots, root tips, pistil, flower, seed and stalks.

13. A pepper plant regenerated from the tissue culture of claim 12, wherein the plant expresses all of the physiological and morphological characteristics of a pepper plant comprising at least a first set of the chromosomes of pepper line SBR99-1243.

14. A method of vegetatively propagating the pepper plant of claim 1 comprising the steps of:
(a) collecting tissue capable of being propagated from a plant according to claim 1;
(b) cultivating said tissue to obtain proliferated shoots; and
(c) rooting said proliferated shoots to obtain rooted pepper plantlets.

15. The method of claim 14, further comprising growing pepper plants from said rooted plantlets.

16. A method of introducing a desired trait into a pepper line comprising:
(a) crossing a plant of pepper line SBR99-1243, a sample of seed of said line having been deposited under ATCC Accession Number PTA-9227, with a second pepper plant that comprises a desired trait to produce F1 progeny;
(b) selecting an F1 progeny that comprises the desired trait;
(c) crossing the selected F1 progeny with a plant of pepper line SBR99-1243 to produce backcross progeny;
(d) selecting backcross progeny comprising the desired trait and the physiological and morphological characteristic of pepper line SBR99-1243; and
(e) repeating steps (c) and (d) three or more times in succession to produce selected fourth or higher backcross progeny that comprise the desired trait.

17. A pepper plant produced by the method of claim 16.

18. A method of producing a pepper plant comprising an added desired trait, the method comprising introducing a transgene conferring the desired trait into a plant of pepper hybrid 9930417 or pepper line SBR99-1243; a sample of seed of said hybrid and line having been deposited under ATCC Accession Number PTA-9223 and ATCC Accession Number PTA-9227, respectively.

19. A method for producing a seed of a pepper plant derived from hybrid 9930417 or pepper line SBR99-1243 comprising the steps of:
(a) crossing a pepper plant of pepper hybrid 9930417 or pepper line SBR99-1243 with a second pepper plant; a sample of seed of said hybrid and line having been deposited under ATCC Accession Number PTA-9223 and ATCC Accession Number PTA-9227, respectively; and
(b) allowing seed of a hybrid 9930417 or line SBR99-1243-derived pepper plant to form.

20. The method of claim 19, further comprising the steps of:
(c) crossing a plant grown from said hybrid 9930417 or line SBR99-1243-derived pepper seed with itself or a second pepper plant to yield additional hybrid 9930417 or line SBR99-1243-derived pepper seed;
(d) growing said additional hybrid 9930417 or line SBR99-1243-derived pepper seed of step (c) to yield additional hybrid 9930417 or line SBR99-1243-derived pepper plants; and
(e) repeating the crossing and growing steps of (c) and (d) to generate further hybrid 9930417 or line SBR99-1243-derived pepper plants.

21. The method of claim 19, wherein the second pepper plant is of an inbred pepper line.

22. The seed of claim 2, defined as seed of pepper hybrid 9930417, a sample of seed of said hybrid 9930417 having been deposited under ATCC Accession Number PTA-9223.

23. A pepper plant produced by growing the seed of claim 22.

24. A pepper plant part of the plant of claim 23.

25. The plant part of claim 24, further defined as a leaf, a flower, a fruit, an ovule, pollen, or a cell.

26. A tissue culture of cells of the pepper plant of claim 23.

27. The tissue culture of claim 26, wherein cells of the tissue culture are from a tissue selected from the group consisting of embryos, meristems, cotyledons, pollen, leaves, anthers, roots, root tips, pistil, flower, seed and stalks.

28. A pepper plant regenerated from the tissue culture of claim 26, wherein the regenerated plant expresses all of the physiological and morphological characteristics of hybrid pepper hybrid 9930417, a sample of seed of said hybrid 9930417 having been deposited under ATCC Accession Number PTA-9223.

29. A pepper seed comprising at least a first set of the chromosomes of pepper line SBR99-1243, wherein the seed further comprises a transgene.

30. A method of producing a pepper fruit comprising:
(a) obtaining a pepper plant according to claim 1, wherein the pepper plant has been cultivated to maturity; and
(b) collecting a pepper from the plant.

31. The method of claim 30, wherein said pepper plant is a plant of pepper hybrid 9930417, a sample of seed of said hybrid 9930417 having been deposited under ATCC Accession Number PTA-9223.

* * * * *